United States Patent
Toeda et al.

(10) Patent No.: US 10,323,155 B2
(45) Date of Patent: Jun. 18, 2019

(54) ACTINIC RADIATION-CURABLE INKJET INK AND IMAGE FORMING METHOD

(71) Applicant: KONICA MINOLTA, INC., Tokyo (JP)

(72) Inventors: Takayuki Toeda, Tokyo (JP); Kana Yamada, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/867,093

(22) Filed: Jan. 10, 2018

(65) Prior Publication Data

US 2018/0223117 A1 Aug. 9, 2018

(30) Foreign Application Priority Data

Feb. 7, 2017 (JP) ................................ 2017-020642

(51) Int. Cl.
| | | |
|---|---|---|
| C08F 2/46 | (2006.01) |
| C08F 2/50 | (2006.01) |
| C08G 61/04 | (2006.01) |
| C09D 11/101 | (2014.01) |
| C09D 11/107 | (2014.01) |
| C07C 69/732 | (2006.01) |
| C07D 263/58 | (2006.01) |
| C07D 333/06 | (2006.01) |
| C09D 11/38 | (2014.01) |

(52) U.S. Cl.
CPC .......... C09D 11/101 (2013.01); C07C 69/732 (2013.01); C07D 263/58 (2013.01); C07D 333/06 (2013.01); C09D 11/107 (2013.01); C09D 11/38 (2013.01)

(58) Field of Classification Search
CPC ..... C09D 11/101; C09D 11/38; C09D 11/107; C07D 333/06; C07D 263/58; C07D 69/732
USPC ............... 522/75, 74, 71, 1, 189, 184; 520/1
See application file for complete search history.

(56) References Cited

U.S. PATENT DOCUMENTS

| | | | |
|---|---|---|---|
| 2012/0029108 A1 | 2/2012 | Nakane et al. | |
| 2012/0062669 A1* | 3/2012 | Keoshkerian | C09D 11/101 347/102 |
| 2012/0225968 A1* | 9/2012 | Nakano | C08F 299/06 522/16 |
| 2013/0335479 A1* | 12/2013 | Takabayashi | C09D 4/00 347/20 |
| 2017/0371122 A1 | 12/2017 | Kouzmina et al. | |

FOREIGN PATENT DOCUMENTS

| | | | |
|---|---|---|---|
| JP | 2006249155 A | 9/2006 | |
| JP | 2006274025 A | 10/2006 | |
| JP | 2009191118 A | 8/2009 | |
| JP | 2011174076 A | 9/2011 | |
| JP | 2011213965 A | 10/2011 | |
| JP | 2012031254 A | 2/2012 | |
| JP | 2012207199 A | 10/2012 | |
| NL | 1998037030 * | 2/1998 | |
| WO | 98/37030 A1 | 8/1998 | |
| WO | WO-2017217187 A1 * | 12/2017 | ............... B41J 2/01 |
| WO | 2018/005329 A1 | 1/2018 | |

OTHER PUBLICATIONS

Frongauz, Machine Translation WO 1998-037030, Feb. 25, 1998 (Year: 1998).*
Toeda, WO 2017217187 Machine Translation, Dec. 21, 2017 (Year: 2017).*
Extended European Search Report dated Apr. 3, 2018 from corresponding European Application No. 17211024.9.
European Office Action dated Dec. 3, 2018 from corresponding European Application No. 17211024.9.

* cited by examiner

*Primary Examiner* — Jessica Whiteley
(74) *Attorney, Agent, or Firm* — Lucas & Mercanti, LLP

(57) ABSTRACT

An actinic radiation-curable inkjet ink containing a photocurable compound, a photopolymerization initiator, a fluorescent brightener, and a phenol-based antioxidant, in which the fluorescent brightener is a compound represented by general formula (1), and the photocurable compound contains a (meth)acrylate having two or more (meth)acryloyl groups in an amount of 80 mass % or more with respect to a total mass of the photocurable compound.

[ Formula 1]

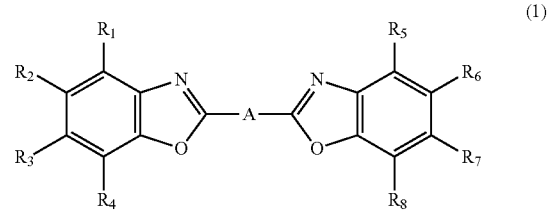

(1)

8 Claims, No Drawings

ACTINIC RADIATION-CURABLE INKJET INK AND IMAGE FORMING METHOD

CROSS REFERENCE TO RELATED APPLICATIONS

Japanese Patent Application No. 2017-020642 filed on Feb. 7, 2017, including description, claims, and abstract the entire disclosure is incorporated herein by reference in its entirety.

BACKGROUND

Technological Field

The present invention relates to an actinic radiation-curable inkjet ink and an image forming method.

Description of Related Art

Formation of images by an inkjet method is employed in various fields of printing because this method is applicable to high-mix low-volume production. As one of image forming methods employing the inkjet method, there is the method in which a droplet of an inkjet ink containing a photocurable compound to be cured through irradiation with actinic radiation (hereinafter sometimes referred to as the "actinic radiation-curable inkjet ink") is caused to land on a substrate, and the droplet of the inkjet ink thus caused to land is cured by irradiation with actinic radiation.

The actinic radiation-curable inkjet ink to be used for this image forming method has been widely studied. For example, Japanese Patent Application Laid-Open Nos. 2006-249155, 2006-274025, 2009-191118, 2011-174076, 2012-207199 and 2012-31254 describe actinic radiation-curable inkjet inks containing a fluorescent brightener. Japanese Patent Application Laid-Open Nos. 2006-274025, 2009-191118, 2011-174076, 2012-207199 and 2012-31254 disclose that the fluorescent brightener increases the curability of the ink, and in particular, Japanese Patent Application Laid-Open Nos. 2009-191118, 2011-174076, 2012-207199 and 2012-31254 also disclose that hue is improved (namely, yellowing is suppressed) by using the fluorescent brightener.

Besides, Japanese Patent Application Laid-Open No. 2011-213965 describes a coating varnish, which is used for increasing the glossiness and the mechanical strength of a printed matter, containing a fluorescent brightener, and the fluorescent brightener is used here for purposes of improving the UV curability of the coating varnish and suppressing yellowing.

Each of the inks described in Japanese Patent Application Laid-Open Nos. 2006-249155, 2006-274025, 2009-191118, 2011-174076, 2012-207199 and 2012-31254 contains the fluorescent brightener. It was found, however, through examinations made by the present inventors that the glossiness of an image is sometimes difficult to increase when the image is formed by using the ink of any of these PTLs. Besides, occurrence of migration was found in such an image.

Furthermore, as a result of the examinations made by the present inventors, the occurrence of migration was found also in an overcoat formed by using the coating varnish of Japanese Patent Application Laid-Open No. 2011-213965.

The present invention was devised in consideration of the above-described problems, and an object is to provide an actinic radiation-curable inkjet ink capable of forming an image having high glossiness with migration suppressed, and an image forming method using the same.

SUMMARY

To achieve at least one of the abovementioned objects, according to an aspect of the present invention, an inkjet ink reflecting one aspect of the present invention is:

an actinic radiation-curable inkjet ink, including a photocurable compound, a polymerization initiator, a fluorescent brightener, and an antioxidant, in which the fluorescent brightener is a compound represented by the following general formula (1):

[Formula 1]

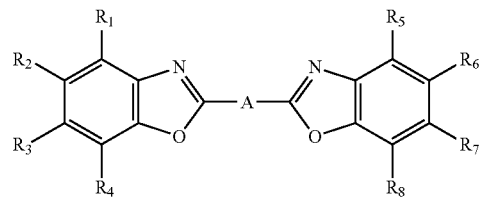

in which $R_1$ to $R_8$ each independently represent a hydrogen atom or an alkyl group, adjacent ones of $R_1$ to $R_8$ optionally forming a ring, and A represents a linking group represented by any one of the following formulas (2) to (5):

[Formula 2]

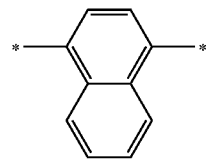

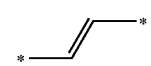

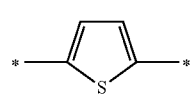

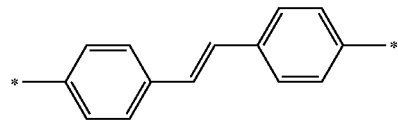

in which each * represents a bonding position of A of each formula;

the antioxidant is a phenol-based antioxidant; and the photocurable compound contains a (meth)acrylate having two or more (meth)acryloyl groups in an amount of 80 mass % or more with respect to a total mass of the photocurable compound.

According to another aspect of the present invention, an image forming method reflecting one aspect of the present invention is:

an image forming method, including: discharging a droplet of the actinic radiation-curable inkjet ink according to a first aspect from a nozzle of an inkjet head and causing the droplet to land on a substrate; and curing the actinic radiation-curable inkjet ink by irradiating, with actinic radiation, the droplet of the actinic radiation-curable inkjet ink landed on the substrate.

DETAILED DESCRIPTION OF EMBODIMENTS

Hereinafter, one or more embodiments of the present invention will be described. However, the scope of the invention is not limited to the disclosed embodiments.

As a result of earnest studies in consideration of the above-described problems, the present inventors have found the following: an inkjet ink containing a fluorescent brightener represented by the following general formula (1), a phenol-based antioxidant, and a photocurable compound containing a (meth)acrylate having two or more (meth) acryloyl groups in an amount of 80 mass % or more with respect to the total mass of the photocurable compound is capable of forming an image having higher glossiness with migration suppressed as compared with an inkjet ink not containing any one of these three components. The reason why these excellent effects can be attained is presumed as follows.

According to novel finding by the present inventors, the fluorescent brightener represented by general formula (1) is easily crystallized when the photocurable compound is polymerized and solidified through irradiation with actinic radiation and hence the concentration of the fluorescent brightener in a liquid component of the actinic radiation-curable inkjet ink increases. The thus crystallized fluorescent brightener forms a smooth layer in the vicinity of the surface of a cured film formed by curing the actinic radiation-curable inkjet ink, and surface irregularities of the cured film are thus reduced, which is considered to increase the glossiness of a resultant image.

Besides, the phenol-based antioxidant is easily aligned with the fluorescent brightener in layers because of π-π interaction between an aromatic ring contained in a molecule thereof and an aromatic ring of the fluorescent brightener represented by general formula (1). It is considered that, owing to this alignment, the phenol-based antioxidant probably further increases the surface area and the smoothness of the layer of the crystallized fluorescent brightener. Besides, when the apparent molecular weight of the crystallized fluorescent brightener increases due to the π-π interaction, the fluorescent brightener and the antioxidant are difficult to pass through a network structure (described later) formed by polymerization and crosslinking of the photocurable compound, which is considered to reduce the migration.

On the other hand, since the fluorescent brightener is not incorporated into a hydrocarbon chain formed through the polymerization and the crosslinking of the photocurable compound, it is easily precipitated (migrated) from the cured film. Besides, when the fluorescent brightener is migrated, the above-described smooth layer is reduced, and hence, the smoothness of the resultant image tends to lower. Furthermore, when the fluorescent brightener is migrated, an effect of suppressing yellowing by the fluorescent brightener is also reduced.

On the contrary, when the proportion of the (meth) acrylate having two or more (meth)acryloyl groups in the photocurable compound is increased, the crosslink density in the cured film is increased to form a denser network structure, and thus, the fluorescent brightener is more difficult to pass through the network structure so that the migration can be suppressed. Besides, when the network structure formed by the crosslinking and the polymerization of the photocurable compound becomes dense, the fluorescent brightener not incorporated into a hydrocarbon chain is easily distributed unevenly in the vicinity of the surface of the cured film during the irradiation with the actinic radiation for curing, which probably more remarkably increases the glossiness caused by the formation of the smooth layer.

In particular, a (meth)acryloyl group is a highly reactive functional group, and hence probably forms a hydrocarbon chain in a denser network shape than another functional group.

The present invention will now be described with reference to exemplary embodiments, and it is noted that the present invention is not limited to the following embodiments.

1. Actinic Radiation-Curable Inkjet Ink

A first embodiment of the present invention is an actinic radiation-curable inkjet ink containing a photocurable compound, a photopolymerization initiator, a fluorescent brightener represented by general formula (1), and a phenol-based antioxidant (hereinafter sometimes simply referred to as the "ink of the present invention"). Herein, the term "actinic radiation" means rays capable of polymerizing and crosslinking the photocurable compound by activating the photopolymerization initiator contained in the ink of the present invention. Examples of the actinic radiation include α-rays, γ-rays, X-rays, ultraviolet rays and electron beams. As the actinic radiation used for curing the ink of the present invention, ultraviolet rays and electron beams are preferably used, and ultraviolet rays are more preferably used from the viewpoint of availability of a radiation emitting apparatus, curability of the ink, and the like.

(1) Photocurable Compound

The photocurable compound is a compound crosslinked or polymerized through irradiation with the actinic radiation. The photocurable compound used in the present invention contains a (meth)acrylate having two or more (meth)acryloyl groups in an amount of 80 mass % or more with respect to the total mass of the photocurable compound.

Herein, the term "(meth)acryloyl" means both acryloyl and methacryloyl, and the term "(meth)acrylate" means both acrylate and methacrylate.

Examples of the (meth)acrylate having two or more (meth)acryloyl groups include difunctional monomers such as triethylene glycol di(meth)acrylate, tetraethylene glycol di(meth)acrylate, polyethylene glycol di(meth)acrylate, tripropylene glycol di(meth)acrylate, polypropylene glycol di(meth)acrylate, 1,4-butanediol di(meth)acrylate, 1,6-hexanediol di(meth)acrylate, 1,9-nonanediol di(meth)acrylate, neopentyl glycol di(meth)acrylate, dimethylol tricyclodecane di(meth)acrylate, bisphenol A PO adduct di(meth) acrylate, neopentyl glycol hydroxypivalate di(meth) acrylate, polytetramethylene glycol di(meth)acrylate, polyethylene glycol diacrylate, tripropylene glycol diacrylate, tricyclodecanedimethanol diacrylate, and 3-methylpentanediol diacrylate; and tri- or higher-functional monomers such as trimethylolpropane tri(meth)acrylate, pentaerythritol tri(meth)acrylate, pentaerythritol tetra(meth)acrylate, dipentaerythritol hexa(meth)acrylate, ditrimethylolpropane tetra (meth)acrylate, glycerin propoxy tri(meth)acrylate, and pentaerythritol ethoxy tetra(meth)acrylate.

A polyfunctional (meth)acrylate is particularly preferably a propylene oxide-modified (meth)acrylate or ethylene oxide-modified (meth)acrylate having been modified with propylene oxide or ethylene oxide. The term "modified with propylene oxide or ethylene oxide" as used herein means that at least one unit of a propylene oxide group or an ethylene oxide group has been introduced into a molecular chain. The number of units of the propylene oxide group or the ethylene oxide group contained in the propylene oxide-modified (meth)acrylate or ethylene oxide-modified (meth) acrylate is preferably 1 or more and 14 or less, and more preferably 3 or more and 14 or less per (meth)acrylate group.

In particular, if the inkjet ink is a gel ink containing a gelling agent described later, the number of units of the propylene oxide group or the ethylene oxide group preferably falls in the above-described range because interaction with the gelling agent can be thus easily caused. Specifically, when the ethylene oxide-modified (meth)acrylate or propylene oxide-modified (meth)acrylate is used in combination with a crystalline gelling agent capable of forming a card house structure, the interaction is caused therebetween to easily form a card house structure, and hence a pinning property of the resultant ink becomes very high. Besides, the ethylene oxide-modified (meth)acrylate and the propylene oxide-modified (meth)acrylate are easily dissolved in another component at a high temperature.

Examples of the ethylene oxide-modified (meth)acrylate include polyethylene glycol di(meth)acrylate, ethylene oxide-modified trimethylolpropane tri(meth)acrylate, ethylene oxide-modified pentaerythritol tetra(meth)acrylate, and ethylene oxide-modified hexanediol diacrylate.

Examples of a commercially available product of the ethylene oxide-modified (meth)acrylate include 4EO modified hexanediol diacrylate CD561 (molecular weight: 358), 3EO modified trimethylolpropane triacrylate SR454 (molecular weight: 429), 6EO modified trimethylolpropane triacrylate SR499 (molecular weight: 560) and 4EO modified pentaerythritol tetraacrylate SR494 (molecular weight: 529), all manufactured by Sartomer; polyethylene glycol #400 diacrylate (NK ester A-400 (molecular weight: 508)), polyethylene glycol #600 diacrylate (NK ester A-600 (molecular weight: 742)), polyethylene glycol dimethacrylate (NK ester 9G (molecular weight: 536)), and polyethylene glycol dimethacrylate (NK ester 14G (molecular weight: 770)), all manufactured by Shin-Nakamura Chemical Co., Ltd.; and tetraethylene glycol diacrylate (V#335HP (molecular weight: 302)), manufactured by Osaka Organic Chemical Industry Ltd.

Examples of the propylene oxide-modified (meth)acrylate include polypropylene glycol di(meth)acrylate, propylene oxide-modified neopentyl glycol di(meth)acrylate, bisphenol A propylene oxide adduct di(meth)acrylate, and glycerin propoxy tri(meth)acrylate.

Examples of a commercially available product of the propylene oxide-modified (meth)acrylate include 3PO modified trimethylolpropane triacrylate (Photomer 4072 (molecular weight: 471)), manufactured by Cognis Corporation; dipropylene glycol diacrylate (NK ester APG-100 (molecular weight: 242)), tripropylene glycol diacrylate (NK ester APG-200 (molecular weight: 300)), polypropylene glycol #400 diacrylate (NK ester APG-400 (molecular weight: 533)), and polypropylene glycol #700 diacrylate (NK ester APG-700 (molecular weight: 823)), all manufactured by Shin-Nakamura Chemical Co., Ltd.; and 6PO modified trimethylolpropane triacrylate CD501 (molecular weight: 645), manufactured by Sartomer.

The ink of the present invention may contain merely one of the above-described polyfunctional monomers, or may contain two or more of these.

The amount of the (meth)acrylate having two or more (meth)acryloyl groups contained in the photocurable compound is 80 mass % or more, preferably 90 mass % or more, and more preferably 95 mass % or more with respect to the total mass of the photocurable compound. The upper limit of the amount of the (meth)acrylate having two or more (meth)acryloyl groups contained in the photocurable compound is not especially limited, and is preferably less than 99 mass %, more preferably less than 100 mass %, and further preferably 100 mass %. A component contained in the photocurable compound in addition to the (meth)acrylate is not especially limited, and examples include a monofunctional (meth)acrylate, and a (meth)acrylate having one (meth)acryloyl group and another functional group.

Examples of the monofunctional (meth)acrylate include monofunctional acrylates including isoamyl (meth)acrylate, stearyl (meth)acrylate, lauryl (meth)acrylate, octyl (meth)acrylate, decyl (meth)acrylate, isomyristyl (meth)acrylate, isostearyl (meth)acrylate, 2-ethyl hexyl-diglycol (meth)acrylate, 2-hydroxybutyl (meth)acrylate, 2-(meth)acryloyloxyethyl hexahydrophthalate, butoxyethyl (meth)acrylate, ethoxy diethylene glycol (meth)acrylate, methoxy diethylene glycol (meth)acrylate, methoxy polyethylene glycol (meth)acrylate, methoxy propylene glycol (meth)acrylate, phenoxy ethyl (meth)acrylate, tetrahydrofurfuryl (meth)acrylate, isobornyl (meth)acrylate, 2-hydroxyethyl (meth)acrylate, 2-hydroxypropyl (meth)acrylate, 2-hydroxy-3-phenoxypropyl (meth)acrylate, 2-(meth)acryloyloxyethyl succinate, 2-(meth)acryloyloxyethyl phthalate, 2-(meth)acryloyloxyethyl-2-hydroxyethyl-phthalic acid, and t-butylcyclohexyl (meth)acrylate.

An example of the (meth)acrylate having one (meth)acryloyl group and another functional group includes 2-(2-vinyloxyethoxy)ethyl acrylate (VEEA).

A content of the photocurable compound in the ink of the present invention is preferably 1 mass % or more and 97 mass % or less, and more preferably 30 mass % or more and 95 mass % or less.

(2) Photopolymerization Initiator

The photopolymerization initiator includes a photo-radical initiator. The ink of the present invention may contain merely one photopolymerization initiator, or a combination of two or more photopolymerization initiators. The photopolymerization initiator may be a combination of a photo-radical initiator and a photoacid generator.

The photo-radical initiator includes a cleavage type radical initiator and a hydrogen abstraction radical initiator.

Examples of the cleavage type radical initiator include acetophenone-based compounds, benzoin-based compounds, acylphosphine-based compounds, benzyl and methyl phenylglyoxylate.

Examples of the hydrogen abstraction radical initiator include α-aminoketone-based compounds, benzophenone-based compounds, thioxanthone-based compounds, aminobenzophenone-based compounds, 10-butyl-2-chloroacridone, 2-ethylanthraquinone, 9,10-phenanthrenequinone, and camphorquinone.

Examples of the photoacid generator include compounds described in "Organic Materials for Imaging", edited by The Japanese Research Association for Organic Electronics Materials, published by Bunshin-Publishing (1993), pp. 187-192.

A content of the photopolymerization initiator may be in the range which the ink of the present invention can be sufficiently cured, and the content can be, for example, 0.01 mass % or more and 10 mass % or less with respect to the total mass of the ink of the present invention.

(3) Fluorescent Brightener

The fluorescent brightener used in the present invention is a benzoxazole-based compound represented by the following general formula (1):

[Formula 3]

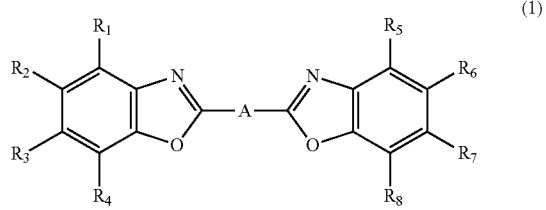

(1)

wherein $R_1$ to $R_8$ each independently represent a hydrogen atom or an alkyl group, $R_1$ to $R_8$ optionally forming a ring; and A represents a linking group represented by any one of the following formulas (2) to (5):

[Formula 4]

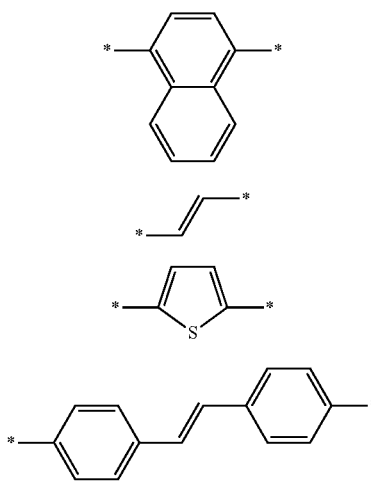

wherein each * represents a bonding position of A of each formula.

In general formula (1), $R_1$ to $R_8$ each independently represent a hydrogen atom or an alkyl group. The alkyl group may be straight, branched or cyclic, and includes an alkyl group having 1 or more and 10 or less carbon atoms. The alkyl group may be substituted, and examples of a substituent used here include a group containing a carbon atom, such as a carboxyl group or an alkoxy group, a hydroxyl group, and a halogen atom.

Since the fluorescent brightener represented by general formula (1) has a lower coloring property than another fluorescent brightener (such as a coumarin-based compound or a stilbene-based compound), the glossiness of an image can be improved with little affecting the color tone of the ink.

Examples of a commercially available product of the benzoxazole-based compound represented by general formula (1) include FLUORESCENT BRIGHTENER KCB (manufactured by Xcolor Pigment) in which A in general formula (1) has the structure of formula (2), FLUORESCENT BRIGHTENER PF (manufactured by Xcolor Pigment) in which A in general formula (1) has the structure of formula (3), FLUORESCENT BRIGHTENER OB and FLUORESCENT BRIGHTENER PB (both manufactured by Xcolor Pigment) in which A in formula (1) has the structure of formula (4), and FLUORESCENT BRIGHTENER OB-1 and FLUORESCENT BRIGHTENER KSN (both manufactured by Xcolor Pigment) in which A in formula (1) has the structure of formula (5).

The fluorescent brightener is contained in an amount of preferably 0.001 mass % or more and 1.2 mass % or less, more preferably 0.01 mass % or more and 0.8 mass % or less, and further preferably 0.1 mass % or more and 0.5 mass % or less with respect to the total mass of the ink of the present invention. From the viewpoint of further reducing coloring with the fluorescent brightener, light source-dependent color change and the like, the amount of the fluorescent brightener to be used preferably falls in the above-described range. Specifically, if the content of the fluorescent brightener is 0.01 mass % or more, the glossiness of a resultant image can be further increased, and if the content of the fluorescent brightener is 1.2 mass % or less, the coloring with the fluorescent brightener and the migration are more difficult to occur.

(4) Antioxidant

The antioxidant used in the present invention is a phenol-based antioxidant.

The phenol-based antioxidant is not limited as long as it has a structure in which one of hydrogen atoms forming an aromatic ring is substituted by a hydroxyl group (hereinafter sometimes simply referred to as the "phenol structure").

The phenol-based antioxidant may be a hindered phenol-based antioxidant having a t-butyl group in (one of or both of) the ortho positions relative to the hydroxyl group, or may be an antioxidant excluding the hindered phenol-based antioxidant.

Besides, the phenol-based antioxidant may contain, in a molecule thereof, an ether group, a thioether group, an ester group, an amide group or the like.

The phenol-based antioxidant may be a monofunctional compound having merely one phenol structure in a molecule, and is preferably a polyfunctional compound having two or more phenol structures in a molecule. The polyfunctional phenol-based antioxidant becomes a crosslinking agent through radical transfer in trapping oxygen contained in the ink of the present invention, so as to increase the density of the network structure by increasing the degree of crosslinking of the photocurable compound, and thus, the migration can be further suppressed.

If the phenol-based antioxidant is a polyfunctional compound, a bonding portion for linking the two or more phenol structures may be positioned in the ortho position relative to the hydroxyl group, or in the para position.

The bonding portion can be an alkyl group, an ether group, a thioether group or the like, and the alkyl group may have a structure in which a plurality of hydrocarbon chains are linked via a thioether group, an ether group, an ester group, an amide group, or an aromatic ring.

An example of the alkyl group includes an alkyl group having 1 or more and 20 or less carbon atoms.

If the phenol-based antioxidant is a polyfunctional compound, the hydroxyl group in any one of the plural phenol structures may form a salt together with (meth)acrylic acid. In this case, however, at least one hydroxyl group not forming the salt is preferably contained.

Examples of the hindered phenol-based antioxidant include [ethylenebis(oxyethylene)]bis[3-(3-tert-butyl-4-hydroxy-5-methylphenyl)propionate], 1,6-hexanediol bis[3-(3,5-di-tert-butyl-4-hydroxyphenyl)propionate], 2,2'-thiodiethyl bis[3-(3,5-di-tert-butyl-4-hydroxyphenyl)propionate], octyl 3,5-di-tert-butyl-4-hydroxy-hydrocinnamate, stearyl 3-(3,5-di-tert-butyl-4-hydroxyphenyl)propionate, pentaerythritol tetrakis[3-(3,5-di-tert-butyl-4-hydroxyphenyl)propionate], 2-tert-butyl-4-methyl-6-(2-hydroxy-3-tert-butyl-3-methylbenzyl)phenyl acrylate, 1'-hydroxy[2,2'-ethylidenebis[4,6-bis(1,1-dimethylpropyl)benzene]]-1-yl acrylate, 2-2'-methylenebis(6-t-butyl-4-methylphenol), 4,4'-butylidenebis(6-tert-butyl-m-cresol), 4,4'-thiobis(6-tert-butyl-m-cresol), 1,1,3-tris(2-methyl-4-hydroxy-5-tert-butylphenyl)butane, N,N'-hexamethylenebis[3-(3,5-di-tert-butyl-4-hydroxyphenyl)propaneamide], 2,4,6-tris(3'-5'-di-tert-butyl-4'-hydroxybenzyl)mesitylene, 1,3,5-tris[[3,5-bis(1,1-dimethylethyl)-4-hydroxyphenyl]methyl]-1,3,5-triazine-2,4,6(1H,3H,5H)-trione, and 3,9-bis[2-[3-(3-tert-butyl-4-hydroxy-5-methylphenyl)propionyloxy]-1,1-dimethylethyl]-2,4,8,10-tetraoxaspiro[5.5]undecane.

An example of the antioxidant excluding the hindered phenol-based antioxidant includes 2,4-bis(octylthiomethyl)-6-methylphenol.

Examples of a commercially available product of the phenol-based antioxidant include IRGANOX 1520L (manufactured by BASF Corporation), NOCRAC NS-6 (manufactured by Ouchi Shinko Chemical Industrial Co., Ltd.), SUMILIZER GS, SUMILIZER GM, SUMILIZER GS(F) and SUMILIZER MDP-S (all manufactured by Sumitomo Chemical Co., Ltd.), Seenox 224M (Shipro Kasei Kaisha Ltd.), IRGANOX 1076, IRGANOX 1330, IRGANOX L109, IRGANOX 1098, IRGANOX 1135 and IRGANOX 3114 (all manufactured by BASF Corporation), ADK STAB AO-20, ADK STAB AO-30, ADK STAB AO-40, ADK STAB AO-50, ADK STAB AO-60, ADK STAB AO-70, ADK STAB AO-80 and ADK STAB AO-330 (all manufactured by ADEKA Corporation), SUMILIZER BBM-S, SUMILIZER WX-R, SUMILIZER WX-RA, SUMILIZER WX-RC and SUMILIZER GA-80 (all manufactured by Sumitomo Chemical Co., Ltd.), and NOCRAC NS-30 and NOCRAC 300 (both manufactured by Ouchi Shinko Chemical Industrial Co., Ltd.).

An antioxidant particularly preferably used is an antioxidant represented by the following general formula (6):

[Formula 5]

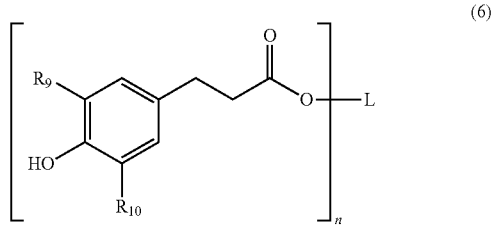

(6)

wherein $R_9$ and $R_{10}$ each independently represent an alkyl group having 1 or more and 4 or less carbon atoms, n represents an integer of 2 to 4, and L represents an alkyl group having 1 or more and 10 or less carbon atoms.

L corresponding to a linking group may have a structure in which a plurality of hydrocarbon chains are linked via a thioether group or an ether group.

Examples of a commercially available product of the antioxidant represented by general formula (6) include IRGANOX 245, IRGANOX 259, IRGANOX L109, IRGANOX 1035 and IRGANOX 1010 (all manufactured by BASF Corporation), and ADK STAB AO-70.

The antioxidant is contained in an amount of preferably 0.05 mass % or more and 1.5 mass % or less, more preferably 0.1 mass % or more and 1.2 mass % or less, and further preferably 0.2 mass % or more and 1.0 mass % or less with respect to the total mass of the ink of the present invention. If the content of the antioxidant is 0.1 mass % or more, color change toward bluish color (i.e., color change in the b* axis negative direction in the CIE L*a*b* color space) caused by fluorescence of the fluorescent brightener is cancelled by yellowing (i.e., color change in the b* axis positive direction in the L*a*b* color space) caused by the antioxidant, and hence, a desired color tone can be easily expressed in an image to be formed. Besides, if the content of the antioxidant is 1.0 mass % or less, the influence of the yellowing caused by the antioxidant is not very large but a desired color tone can be easily expressed in an image to be formed.

(5) Gelling Agent

The ink of the present invention may contain a gelling agent. The gelling agent can temporarily fix an ink droplet caused to land on a recording medium by gelling the droplet. When an ink is pinned in a gel state, wet-spreading of the ink is suppressed to prevent adjacent dots from combining each other, and therefore, a higher resolution image can be formed. Besides, when an ink is in a gel state, entrance of environmental oxygen into an ink droplet is suppressed to prevent curing inhibition otherwise caused by the oxygen, and therefore, a high resolution image can be formed in higher speed.

On the contrary to these effects, an image formed by using an ink containing a gelling agent tends to be degraded in glossiness on the surface thereof in general. When an ink containing a gelling agent lands on a substrate, it is crystallized through cooling, and it is presumed that the crystal of the gelling agent is not incorporated into a polymer chain of a photocurable compound formed through the irradiation with the actinic radiation (such as ultraviolet rays) or the like, but partly moves to the vicinity of the surface of a cured film. Therefore, if the crystal structure is too large, irregularities caused on the surface of the cured film are probably increased to degrade the glossiness of a resultant image.

In the inkjet ink of the present invention containing the fluorescent brightener represented by general formula (1), the phenol-based antioxidant, and the photocurable compound containing the (meth)acrylate having two or more (meth)acryloyl groups in an amount of 80 mass % or more with respect to the total mass of the photocurable compound, however, even if a gelling agent is contained, the glossiness of an image to be formed can be increased. The reason is not clear but may be owing to the following effect of the fluorescent brightener in addition to the aforementioned increase of the glossiness caused by the use of the three components.

When the polymerization of the photocurable compound proceeds through the irradiation, with the actinic radiation, of the ink containing the fluorescent brightener and the gelling agent, the amount of the photocurable compound (monomer) is reduced, and hence the concentration of the fluorescent brightener relatively increases. When the concentration of the fluorescent brightener exceeds its solubility, the fluorescent brightener is crystallized. At this point, the crystal of the fluorescent brightener wedges into voids or the like of the card house structure precedently formed by the crystal of the gelling agent so as to make the crystal structure fine. As a result, the crystal size of the gelling agent moving to the vicinity of the surface of the cured film is reduced, and hence the irregularities caused on the surface of the cured film are reduced, which probably increases the glossiness of a resultant image.

It is noted that the ink may contain merely one gelling agent, or may contain two or more gelling agents.

A content of the gelling agent is preferably 1.0 mass % or more and 10.0 mass % or less with respect to the total mass of the ink. If the content of the gelling agent is 1.0 mass % or more, the pinning property of the ink can be improved. When an image is formed on a water-absorbent substrate in particular, insufficient coloring otherwise caused because the ink permeates into the substrate can be made difficult to occur, and an image in a desired color gamut can be easily formed. If the content of the gelling agent is 10.0 mass % or less, the gelling agent is difficult to precipitate on the surface of a resultant image, the glossiness of the image can be made closer to the glossiness of an image formed with another ink, and an ink discharging property from an inkjet head can be further increased. From these points of view, the content of the gelling agent in the ink is preferably 1.0 mass % or more and 7.0 mass % or less, more preferably 1.0 mass % or more and 5.0 mass % or less, and further preferably 1.5 mass % or more and 4.0 mass % or less.

Besides, from the following viewpoint, the gelling agent is crystallized in the ink preferably at a temperature equal to or lower than a gelling temperature of the ink. A gelling temperature refers to a temperature at which, in cooling an ink having been solated or liquefied by heating, a gelling agent undergoes a phase transition from a sol to a gel and the viscosity of the ink is abruptly changed. Specifically, a solated or liquefied ink is cooled with its viscosity measured with a viscoelasticity measuring device (such as MCR300, manufactured by Physica), and a temperature at which the viscosity abruptly increases can be defined as the gelling temperature of the ink.

When the gelling agent is crystallized in the ink, a structure in which the photocurable compound is embraced in a three-dimensional space formed by the gelling agent crystallized in a plate shape (which structure is hereinafter referred to as the "card house structure") is formed in some cases. When the card house structure is formed, the photocurable compound in a liquid form is held within the space, the wet-spreading of the ink droplet is more difficult to occur, and hence the pinning property of the ink further increases. When the pinning property of the ink increases, ink droplets caused to land on a recording medium are difficult to combine with each other, and hence, a higher resolution image can be formed.

In order to form the card house structure, the photocurable compound and the gelling agent dissolved in the ink are preferably compatibilized with each other. On the contrary, if the photocurable compound and the gelling agent dissolved in the ink are separated in phase, the card house structure is difficult to form in some cases.

Examples of the gelling agent suitably used for forming the card house structure through the crystallization include a ketone wax, an ester wax, a petroleum wax, a vegetable wax, an animal wax, a mineral wax, a hydrogenated castor oil, a modified wax, a higher fatty acid, a higher alcohol, hydroxystearic acid, fatty acid amides including N-substituted fatty acid amide and special fatty acid amide, a higher amine, a sucrose fatty acid ester, a synthetic wax, dibenzylidene sorbitol, dimer acid, and dimer diol.

Examples of the ketone wax include dilignoceryl ketone, dibehenyl ketone, distearyl ketone, dieicosyl ketone, dipalmityl ketone, dilauryl ketone, dimyristyl ketone, myristyl palmityl ketone, and palmityl stearyl ketone.

Examples of the ester wax include behenyl behenate, icosyl icosanoate, stearyl stearate, palmityl stearate, cetyl palmitate, myristyl myristate, cetyl myristate, myristyl cerotate, oleyl palmitate, glycerin fatty acid ester, sorbitan fatty acid ester, propylene glycol fatty acid ester, ethylene glycol fatty acid ester, and polyoxyethylene fatty acid ester.

Examples of a commercially available product of the ester wax include EMALEX series, manufactured by Nihon Emulsion Co., Ltd. ("EMALEX" being their registered trademark), and RIKEMAL series and POEM series, manufactured by Riken Vitamin Co., Ltd. (both "RIKEMAL" and "POEM" being their registered trademarks).

Examples of the petroleum wax include a paraffin wax, a microcrystalline wax, and a petrolactam.

Examples of the vegetable wax include a candelilla wax, a carnauba wax, a rice wax, a Japan wax, a jojoba oil, a jojoba solid wax, and a jojoba ester.

Examples of the animal wax include a beeswax, a lanolin, and a spermaceti.

Examples of the mineral wax include montan wax and hydrogenated wax.

Examples of the modified wax include a montan wax derivative, a paraffin wax derivative, a microcrystalline wax derivative, a 12-hydroxystearate derivative, and a polyethylene wax derivative.

Examples of the higher fatty acid include behenic acid, arachidic acid, stearic acid, palmitic acid, myristic acid, lauric acid, oleic acid, and erucic acid.

Examples of the higher alcohol include stearyl alcohol and behenyl alcohol.

An example of the hydroxystearic acid includes 12-hydroxystearic acid.

Examples of the fatty acid amides include lauric acid amide, stearic acid amide, behenic acid amide, oleic acid amide, erucic acid amide, ricinoleic acid amide, and 12-hydroxystearic acid amide.

Examples of a commercially available product of the fatty acid amide include NIKKAMIDE series, manufactured by Nippon Kasei Chemical Co., Ltd. ("NIKKAMIDE" being their registered trademark), ITOWAX series, manufactured by Ito Oil Chemicals Co., Ltd., and FATTY AMID series, manufactured by Kao Corporation.

Examples of the N-substituted fatty acid amide include N-stearyl stearic acid amide, and N-oleyl palmitic acid amide.

Examples of the special fatty acid amide include N,N'-ethylenebis stearyl amide, N,N'-ethylenebis-12-hydroxy stearyl amide, and N,N'-xylylenebis stearyl amide.

Examples of the higher amine include dodecylamine, tetradecylamine, and octadecylamine.

Examples of the sucrose fatty acid ester include sucrose stearate and sucrose palmitate.

Examples of a commercially available product of the sucrose fatty acid ester include RYOTO sugar ester series, manufactured by Mitsubishi-Chemical Foods Corporation ("RYOTO" being their registered trademark).

Examples of the synthetic wax include a polyethylene wax, and an α-olefin maleic anhydride copolymer wax.

Examples of a commercially available product of the synthetic wax include UNILIN series, manufactured by Baker-Petrolite ("UNILIN" being their registered trademark).

An example of the dibenzylidene sorbitol includes 1,3:2, 4-bis-O-benzylidene-D-glucitol.

An example of a commercially available product of the dibenzylidene sorbitol includes GEL ALL D, manufactured by New Japan Chemical Co., Ltd. ("GEL ALL" being their registered trademark).

Examples of a commercially available product of the dimer diol include PRIPOR series, manufactured by CRODA ("PRIPOR" being their registered trademark).

Among these gelling agents, a ketone wax represented by the following general formula (G1) and an ester wax represented by the following general formula (G2) are further preferred. It is presumed that when the ketone wax or the ester wax is used together with the photocurable compound containing the (meth)acrylate having two or more (meth)acryloyl groups in an amount of 80 mass % or more with respect to the total mass of the photocurable compound, the card house structure can be easily formed, and the pinning performance of the ink is improved.

The ink may contain merely one of, or two or more of each of the ketone waxes represented by general formula (G1) and the ester waxes represented by general formula (G2). Besides, the ink may contain either one of or both of the ketone wax represented by general formula (G1) and the ester wax represented by general formula (G2).

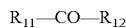  General Formula (G1):

In general formula (G1), each of $R_{11}$ and $R_{12}$ represents a straight chain hydrocarbon group having 9 or more and 25 or less carbon atoms. This hydrocarbon group may have a branched chain.

  General formula (G2):

In general formula (G2), each of $R_{13}$ and $R_{14}$ represents a straight chain hydrocarbon group having 9 or more and 25 or less carbon atoms. This hydrocarbon group may have a branched chain.

In the ketone wax represented by general formula (G1) and the ester wax represented by general formula (G2), the carbon number of a straight chain or branched chain hydrocarbon group is 9 or more, and therefore, the crystallinity of the gelling agent further increases, and a more sufficient space is formed in the card house structure. Therefore, the photocurable compound can be easily sufficiently embraced in the space, and the pinning property of the ink further increases. Besides, since the carbon number of the straight chain or branched chain hydrocarbon group is 25 or less, the melting point of the gelling agent does not excessively increase, and hence there is no need to excessively heat the ink in discharging the ink. From the above-described points of view, each of $R_{11}$ and $R_{12}$ is particularly preferably a straight chain hydrocarbon group having 11 or more and less than 23 carbon atoms.

Besides, from the viewpoint of rapidly gelling the ink after the landing by increasing the gelling temperature of the ink, either one of $R_{11}$ and $R_{12}$, or either one of $R_{13}$ and $R_{14}$ is preferably a saturated hydrocarbon group having 11 or more and less than 23 carbon atoms. From the above-described viewpoint, both of $R_{11}$ and $R_{12}$, or both of $R_{13}$ and $R_{14}$ are preferably saturated hydrocarbon groups having 11 or more and less than 23 carbon atoms.

Examples of the ketone wax represented by general formula (G1) include dilignoceryl ketone (carbon numbers: 23-24), dibehenyl ketone (carbon numbers: 21-22), distearyl ketone (carbon numbers: 17-18), dieicosyl ketone (carbon numbers: 19-20), dipalmityl ketone (carbon numbers: 15-16), dimyristyl ketone (carbon numbers: 13-14), dilauryl ketone (carbon numbers: 11-12), lauryl myristyl ketone (carbon numbers: 11-14), lauryl palmityl ketone (carbon numbers: 11-16), myristyl palmityl ketone (carbon numbers: 13-16), myristyl stearyl ketone (carbon numbers: 13-18), myristyl behenyl ketone (carbon numbers: 13-22), palmityl stearyl ketone (carbon numbers: 15-18), palmityl behenyl ketone (carbon numbers: 15-22), and stearyl behenyl ketone (carbon numbers: 17-22). It is noted that the carbon numbers in parentheses correspond to carbon numbers (the number of carbon atoms) of two hydrocarbon groups divided by a carbonyl group.

Examples of a commercially available product of the ketone wax represented by general formula (G1) include 18-Pentatriacontanon, manufactured by Alfa Aesar, Hentriacontan-16-on, manufactured by Alfa Aesar, and Kao Wax T1, manufactured by Kao Corporation.

Examples of the fatty acid or the ester wax represented by general formula (G2) include behenyl behenate (carbon numbers: 21-22), icosyl icosanoate (carbon numbers: 19-20), stearyl stearate (carbon numbers: 17-18), palmityl stearate (carbon numbers: 17-16), lauryl stearate (carbon numbers: 17-12), cetyl palmitate (carbon numbers: 15-16), stearyl palmitate (carbon numbers: 15-18), myristyl myristate (carbon numbers: 13-14), cetyl myristate (carbon numbers: 13-16), octyldodecyl myristate (carbon numbers: 13-20), stearyl oleate (carbon numbers: 17-18), stearyl erucate (carbon numbers: 21-18), stearyl linoleate (carbon numbers: 17-18), behenyl oleate (carbon numbers: 18-22), and arachidyl linoleate (carbon numbers: 17-20). It is noted that the carbon numbers in parentheses correspond to carbon numbers of two hydrocarbon groups divided by a carbonyl group.

Examples of a commercially available product of the ester wax represented by general formula (G2) include UNISTER M-2222SL and SPERMACETI, manufactured by NOF Corporation ("UNISTER" being their registered trademark), Exepearl SS and Exepearl MY-M, manufactured by Kao Corporation ("Exepearl" being their registered trademark), EMALEX CC-18 and EMALEX CC-10, manufactured by Nihon Emulsion Co., Ltd. ("EMALEX" being their registered trademark), and AMREPS PC, manufactured by Kokyu Alcohol Kogyo Co., Ltd. ("AMREPS" being their registered trademark). Many of these commercially available products are mixtures of two or more components, and hence, they may be separated and refined if necessary before the addition to the ink.

(6) Additional Components

The ink of the present invention may further contain other components including a colorant, a photopolymerization initiator auxiliary agent, a polymerization inhibitor and the like. The ink of the present invention may contain merely one of these components, or two or more of these.

The colorant can be a dye or a pigment, and a pigment is preferably used because a pigment has good dispersibility in the components of the ink and is excellent in weather resistance. The pigment is not especially limited, and can be, for example, any of organic pigments or inorganic pigments of the following numbers listed in Color Index:

Examples of red or magenta pigments include Pigment Red 3, 5, 19, 22, 31, 38, 43, 48:1, 48:2, 48:3, 48:4, 48:5, 49:1, 53:1, 57:1, 57:2, 58:4, 63:1, 81, 81:1, 81:2, 81:3, 81:4, 88, 104, 108, 112, 122, 123, 144, 146, 149, 166, 168, 169, 170, 177, 178, 179, 184, 185, 208, 216, 226, 257, Pigment Violet 3, 19, 23, 29, 30, 37, 50, 88, Pigment Orange 13, 16, 20, 36, and a mixture thereof.

Examples of blue or cyan pigments include Pigment Blue 1, 15, 15:1, 15:2, 15:3, 15:4, 15:6, 16, 17:1, 22, 27, 28, 29, 36, 60, and a mixture thereof.

Examples of green pigments include Pigment Green 7, 26, 36, 50, and a mixture thereof. Examples of yellow pigments include Pigment Yellow 1, 3, 12, 13, 14, 17, 34, 35, 37, 55, 74, 81, 83, 93, 94, 95, 97, 108, 109, 110, 137, 138, 139, 153, 154, 155, 157, 166, 167, 168, 180, 185, 193, and a mixture thereof.

Examples of black pigments include Pigment Black 7, 28, 26, and a mixture thereof.

Examples of commercially available products of the pigments include Chromofine Yellow 2080, 5900, 5930, AF-1300, 2700L, Chromofine Orange 3700L, 6730, Chromofine Scarlet 6750, Chromofine Magenta 6880, 6886, 6891N, 6790, 6887, Chromofine Violet RE, Chromofine Red 6820, 6830, Chromofine Blue HS-3, 5187, 5108, 5197, 5085N, SR-5020, 5026, 5050, 4920, 4927, 4937, 4824, 4933GN-EP, 4940, 4973, 5205, 5208, 5214, 5221, 5000P, Chromofine Green 2GN, 2GO, 2G-550D, 5310, 5370, 6830, Chromofine Black A-1103, SEIKAFAST YELLOW 10GH, A-3, 2035, 2054, 2200, 2270, 2300, 2400(B), 2500, 2600, ZAY-260, 2700(B), 2770, SEIKAFAST RED 8040, C405 (F), CA 120, LR-116, 1531B, 8060R, 1547, ZAW-262, 1537B, GY, 4R-4016, 3820, 3891, ZA-215, SEIKAFAST CARMINE 6B1476T-7, 1483LT, 3840, 3870, SEIKAFAST BORDEAUX 10B-430, SEIKALIGHT ROSE R40, SEIKALIGHT VIOLET B 800, 7805, SEIKAFAST MAROON 460N, SEIKAFAST ORANGE 900, 2900, SEIKALIGHT BLUE C 718, A 612, Cyanine Blue 4933M, 4933GN-EP, 4940, 4973 (from Dainichiseika Color & Chemicals Mfg. Co., Ltd.); KET Yellow 401, 402, 403, 404, 405, 406, 416, 424, KET Orange 501, KET Red 301, 302, 303, 304, 305, 306, 307, 308, 309, 310, 336, 337, 338, 346, KET Blue 101, 102, 103, 104, 105, 106, 111, 118, 124, KET Green 201 (from Dainippon Ink & Chemicals Inc.); Colortex Yellow 301, 314, 315, 316, P-624, 314, U10GN, U3GN, UNN, UA-414, U263, Finecol Yellow T-13, T-05, Pigment Yellow 1705, Colortex Orange 202, Colortex Red 101, 103, 115, 116, D3B, P-625, 102, H-1024, 105C, UFN, UCN, UBN, U3BN, URN, UGN, UG276, U456, U457, 105C, USN, Colortex Maroon 601, Colortex Brown B610N, Colortex Violet 600, Pigment Red 122, Colortex Blue 516, 517, 518, 519, A818, P-908, 510, Colortex Green 402, 403, Colortex Black 702, U905 (from Sanyo Color Works, Ltd.); Lionol Yellow 1405G, Lionol Blue FG7330, FG7350, FG7400G, FG7405G, ES, ESP-S (from Toyo Ink Co., Ltd.); Toner Magenta E 02, Permanent Rubin F6B, Toner Yellow HG, Permanent Yellow GG-02, Hostaperm Blue B2G (from Hoechst AG); Novoperm P-HG, Hostaperm Pink E, Hostaperm Blue B2G (from Clariant); Carbon Black #2600, #2400, #2350, #2200, #1000, #990, #980, #970, #960, #950, #850, MCF 88, #750, #650, MA600, MA7, MA8, MA11, MA100, MA100R, MA77, #52, #50, #47, #45, #45L, #40, #33, #32, #30, #25, #20, #10, #5, #44, and CF9 (from Mitsubishi Chemical Corporation).

A volume average particle size of a pigment particle contained in the ink is preferably 0.08 to 0.5 µm, and a maximum particle size thereof is preferably 0.3 to 10 µm, and more preferably 0.3 to 3 µm. An average particle size of a pigment particle means a value obtained by a dynamic light scattering method using Zetasizer Nano ZSP, manufactured by Malvern Instruments. Incidentally, since an ink containing a colorant has such a high concentration that light is not transmitted therethrough in using this measuring apparatus, the ink is diluted 200 times before the measurement. A measurement temperature is set to normal temperature (25° C.).

A content of the colorant is preferably 0.1 mass % or more and 20 mass % or less, and more preferably 0.4 mass % or more and 10 mass % or less with respect to the total mass of the ink.

Besides, if the ink contains the pigment, the ink may contain a pigment dispersant for dispersing the pigment. If the ink contains a pigment dispersant, the dispersibility of the pigment is improved.

The ink of the present invention may further contain a dispersing auxiliary agent if necessary. As the dispersing auxiliary agent, any of known compounds is appropriately selected in accordance with the pigment. A content of the pigment dispersant and the dispersing auxiliary agent is preferably 1 to 50 mass % with respect to the total mass of the pigment.

The photopolymerization initiator auxiliary agent can be a tertiary amine compound, and is particularly preferably an aromatic tertiary amine compound. Examples of the aromatic tertiary amine compound include N,N-dimethylaniline, N,N-diethylaniline, N,N-dimethyl-p-toluidine, ethyl N,N-dimethylamino-p-benzoate, isoamylethyl N,N-dimethylamino-p-benzoate, N,N-dihydroxyethyl aniline, triethylamine and N,N-dimethylhexylamine. Among these, ethyl N,N-dimethylamino-p-benzoate and isoamylethyl N,N-dimethylamino-p-benzoate are preferably used. The ink of the present invention may contain merely one of these photopolymerization initiator auxiliary agents, or two or more of these. An example of a commercially available product of the photopolymerization initiator auxiliary agent includes SPEEDCURE 7040, manufactured by Lamb son.

A content of the photopolymerization initiator auxiliary agent is preferably 0.1 mass % or more and 5 mass % or less with respect to the total mass of the ink. If the amount of the photopolymerization initiator auxiliary agent falls in the above-described range, the curability of the ink becomes good.

Examples of the polymerization inhibitor include (alkyl) phenol, hydroquinone, catechol, resorcin, p-methoxyphenol, t-butylcatechol, t-butylhydroquinone, pyrogallol, 1,1-picrylhydrazyl, phenothiazine, p-benzoquinone, nitrosobenzene, 2,5-di-t-butyl-p-benzoquinone, dithiobenzoyl disulfide, picric acid, cupferron, aluminum N-nitrosophenylhydroxylamine, tri-p-nitrophenylmethyl, N-(3-oxyanilino-1,3-dimethylbutylidene)aniline oxide, dibutyl cresol, cyclohexanone oxime cresol, guaiacol, o-isopropylphenol, butyraldoxime, methyl ethyl ketoxime, and cyclohexanone oxime. An example of a commercially available product of the polymerization inhibitor includes Irgastab UV10, manufactured by BASF Corporation.

A content of the polymerization inhibitor is preferably 0.001 mass % or more and 0.2 mass % or less with respect to the total mass of the ink. If the amount of the polymerization inhibitor falls in this range, the resultant ink attains good storage stability.

Besides, the ink of the present invention may contain a ultraviolet absorber, an antioxidant or the like from the viewpoint of improving the weather resistance of the cured film. Any of known compounds can be used as the ultraviolet absorber, and from the viewpoint of the weather resistance and ozone resistance, one having the longer wavelength end of the absorption wavelength of 410 nm or less is preferably used. The absorption wavelength of the ultraviolet absorber can be obtained by measuring a ultraviolet and visible absorption spectrum. A content of the ultraviolet absorber is preferably 2 mass % or less, more preferably 1 mass % or less, and further preferably 0.5 mass % or less with respect to the total mass of the ink from the viewpoint of the curability. On the other hand, from the viewpoint of absorbing ultraviolet rays irradiating from the environment (sunlight and lighting) to increase light resistance of the cured film, the content of the ultraviolet absorber is preferably 0.1 mass % or more with respect to the total mass of the ink.

The ink of the present invention may further contain any of various additives and resins in addition to those described above if necessary. Examples of the various additives include a surfactant, a leveling additive, a matting agent, an infrared absorber, an antibacterial agent, and a basic compound for improving the storage stability of the ink. Examples of the basic compound include basic alkali metal compounds, basic alkali earth metal compounds, and basic organic compounds such as amine.

A content of the various additives such as a surfactant is preferably 1 mass % or less, and more preferably 0.5 mass % or less with respect to the total mass of the ink from the viewpoint of making the fluorescent brightener (and the gelling agent) easily crystallized.

Examples of the resins include resins for adjusting the physical properties of the cured film, and specifically include polyester-based resins, polyurethane-based resins, vinyl-based resins, acrylic-based resins and rubber-based resins.

1-5. Physical Properties

In order to further increase an ink discharging property from an inkjet head, the ink of the present invention has a viscosity at 80° C. of preferably 3 mPa·s or more and 20 mPa·s or less. Besides, from the viewpoint of sufficiently gelling the ink caused to land and cooled to normal temperature, the ink of the present invention has a viscosity at 25° of preferably 1,000 mPa·s or more.

If the ink of the present invention is a gel ink containing a gelling agent, the gelling temperature is preferably 40° C. or more and less than 100° C. If the gelling temperature of the ink is 40° C. or more, the ink is rapidly gelled after the landing on a substrate, and hence the pinning property further increases. If the gelling temperature of the ink is less than 100° C., the ink having been gelled by heating can be discharged from the inkjet head, and hence the ink can be more stably discharged. From the viewpoint of reducing the load on an image forming apparatus by making the ink dischargeable at a lower temperature, the gelling temperature of the ink of the present invention is more preferably 40° C. or more and less than 70° C.

The viscosity at 80° C., the viscosity at 25° C. and the gelling temperature of the ink of the present invention can be obtained by measuring, with a rheometer, change, with temperature, of dynamic viscoelasticity of the ink. In the present invention, these viscosities and the gelling temperature are obtained by the following methods: The ink of the present invention is heated to 100° C., and while measuring its viscosity with a stress-controlled rheometer, Physica MCR301 (diameter of cone plate: 75 mm, cone angle: 1.0°), manufactured by Anton Paar, the ink is cooled to 20° C. under conditions of a shear rate of 11.7 (Vs) and a cooling rate of 0.1° C./s, and thus, a viscosity-temperature curve is obtained. The viscosity at 80° C. and the viscosity at 25° C. can be obtained reading viscosities at 80° C. and 25° C. on the viscosity-temperature curve. The gelling temperature can be obtained as a temperature at which the viscosity is 200 mPa·s on the viscosity-temperature curve.

2. Image Forming Method

A second embodiment of the present invention is an image forming method using the ink of the present invention.

The image forming method of the present invention can be carried out in the same manner as a known image forming method in which an actinic radiation-curable inkjet ink is discharged from an inkjet head to land and be cured on a substrate except that the above-described actinic radiation-curable inkjet ink is used.

The image forming method of the present invention includes, for example, a first step of causing the ink of the present invention to be ejected from a nozzle of an inkjet head and to land on a substrate; and a second step of curing the ink by irradiating the ink thus caused to land with actinic radiation.

(1) First Step

In the first step, a droplet of the ink of the present invention is discharged from the inkjet head, so as to cause the droplet to land on a substrate in a position according to an image to be formed.

As a discharging method from the inkjet head, either of a drop-on-demand method or a continuous method may be employed. In employing the drop-on-demand method, the inkjet head may be any one of a single cavity type, a double cavity type, a vendor type, a piston type, an electrical/mechanical conversion system such as a share mode type or a shared wall type, and an electrical/thermal conversion system such as a thermal inkjet type or a bubble-jet type ("bubble-jet" being a registered trademark of Canon Inc.).

Discharging stability of the ink droplet can be increased, particularly when the ink of the present invention is a gel ink, by discharging the droplet in a heated state from the inkjet head. The temperature of the ink in discharging is preferably 35° C. or more and 100° C. or less, and for further increasing the discharging stability, is more preferably 35° C. or more and 80° C. or less. In particular, the droplet is preferably ejected at an ink temperature at which the viscosity of the ink is 7 mPa·s or more and 15 mPa·s or less, and more preferably 8 mPa·s or more and 13 mPa·s or less.

If the ink of the present invention is a gel ink containing a gelling agent, in order to improve an ejecting property of the ink of the present invention from a discharge recording head, the temperature of the ink of the present invention filled in the discharge recording head is preferably set to a range from [the gelling temperature of the ink+10° C.] to [the gelling temperature+30° C.]. If the temperature of the ink of the present invention held in the discharge recording head is lower than [the gelling temperature+10° C.], the ink tends to be gelled within the discharge recording head or on a surface of a nozzle to lower the ejecting property of the ink of the present invention. On the other hand, if the temperature of the ink of the present invention held in the discharge recording head exceeds [the gelling temperature+30° C.], the temperature of the ink is so high that the ink components may be degraded.

A method for heating the ink of the present invention to a prescribed temperature is not especially limited. For example, at least any one of an ink tank included in a head carriage, an ink supply system such as a supply pipe or an anterior chamber immediately before a head, a pipe with a filter, and a piezo head can be heated to a prescribed temperature by using any one of a panel heater, a ribbon heater, heating water and the like.

The amount of the droplet of the ink of the present invention to be discharged is preferably 2 pL or more and 20 pL or less from the viewpoint of a recording rate and an image quality.

The substrate is not especially limited, and general paper such as non-coated paper, coated paper and cardboard, synthetic paper, various plastics used for soft packaging and films thereof can be used. Examples of the various plastic films include a PP film, a PET film, an OPS film, an OPP film, an ONy film, a PVC film, a PE film and a TAC film. Examples of other plastics include polycarbonate, an acrylic resin, ABS, polyacetal, PVA and rubbers. Alternatively, a metal or a glass is applicable. Incidentally, the ink of the present invention is capable of forming an image with higher glossiness than a conventional ink, and therefore, coated paper or the like with comparatively high glossiness is suitably used.

If the ink of the present invention is a gel ink containing a gelling agent, the temperature of the substrate at the time of the ink droplet landing is preferably controlled to 20° C. or more and 40° C. or less from the viewpoint of the gelation of the ink.

(2) Second Step

In the second step, the droplet of the ink of the present invention caused to land in the first step is irradiated with the actinic radiation to form an image by curing the ink of the present invention. The actinic radiation is irradiated preferably within 0.001 seconds or more and 1.0 second or less after the landing of the ink, and for forming a high resolution image, more preferably within 0.001 seconds or more and 0.5 seconds or less.

The actinic radiation used for irradiating the ink can be selected from, for example, electron beams, ultraviolet rays, α-rays, γ-rays and X-rays, and among these, ultraviolet rays are preferably used for the irradiation. The ultraviolet rays can be irradiated, for example, using a water-cooled LED of 395 nm, manufactured by Phoseon Technology, Inc. When an LED is used as a light source, occurrence of ink curing failure otherwise caused because the ink is melted by radiant heat of the light source can be suppressed.

The LED light source is installed so that peak illuminance of the ultraviolet rays of a wavelength of 370 nm or more and 410 nm or less on an image surface can be 0.5 W/cm$^2$ or more and 10 W/cm$^2$ or less, and more preferably 1 W/cm$^2$ or more and 5 W/cm$^2$ or less. From the viewpoint of suppressing the radiant heat irradiating the ink, the amount of radiation used for irradiating an image is preferably less than 350 mJ/cm$^2$.

Besides, the irradiation with the actinic radiation can be carried out in two steps as follows: First, the actinic radiation is irradiated as described above within 0.01 seconds or more and 2.0 seconds or less after the landing of the ink of the present invention for temporarily curing the ink of the present invention, and after completing the irradiation for the whole image, the actinic radiation is further irradiated so as to finally cure the ink of the present invention. If the irradiation with the actinic radiation is thus carried out in the two steps, shrinkage of a recording material, which may occur in curing the ink, can be further suppressed.

In the image forming method of the present invention, if a total ink thickness obtained after curing the ink of the present invention caused to land on the substrate through the irradiation with the actinic radiation is 2 μm or more and 20 μm or less, occurrence of curl and wrinkle of the substrate, change in texture of the substrate, and the like can be more efficiently prevented. It is noted that the term "total ink thickness" means a sum of thicknesses of all inks applied or printed on the substrate, or an average value of the thicknesses measured in a plurality of points where the amount of ink caused to land is estimated to be large.

EXAMPLES

The present invention will now be described with reference to examples, and it is noted that the present invention is not limited to these examples. Incidentally, the term "part" or "%" used in the examples means "part by mass" or "mass %" unless otherwise defined.

1. Preparation of Ink 1-1. Preparation of Cyan Pigment Dispersion

A cyan pigment dispersion was prepared as follows:

A stainless steel beaker was charged with 9 mass % of EFKA4130 (manufactured by BASF Corporation) used as a pigment dispersant, and 71 mass % of tricyclodecanedimethanol diacrylate (A-DCP: manufactured by Shin-Nakamura Chemical Co., Ltd.) used as a photocurable compound (polyfunctional monomer), and the resultant was stirred for 1 hour with heating on a hot plate at 65° C.

The thus obtained mixture was cooled to room temperature, and 20 mass % of Pigment Blue 15:4 (manufactured by Dainichiseika Color & Chemicals Mfg. Co., Ltd.) used as a pigment was added thereto. The resultant solution was put in a glass bottle together with 200 g of zirconia beads having a diameter of 0.5 mm, and the glass bottle was tightly sealed and subjected to a dispersion treatment with a paint shaker for 5 hours. Thereafter, the zirconia beads were removed to obtain a cyan pigment dispersion.

1-2. Preparation of Ink

In accordance with ink components shown in Tables 1 to 6 below, the above-described pigment dispersion was mixed with the following components, and the resultant was heated to 80° C. and stirred. The thus obtained mixture was filtered, with heating, through a Teflon® 3 μm-membrane filter manufactured by ADVANTEC Co., Ltd. to obtain each of ink samples 1 to 31. Tables 1 to 6 below show a content of each component with a rounded value, and the amount of MPDDA was controlled so that the total amount of the ink be 100 mass %. It is noted that the amount of each component shown in these tables is in mass %.

(Ink Materials)
[Photocurable Compound]
(Polyfunctional (Meth)acrylate Monomer)
3-Methylpentanediol diacrylate (MPDDA)
Propylene oxide (PO)-modified neopentyl glycol diacrylate (PO-NPGDA)
Polyethylene glycol #400 diacrylate (PEG400DA) (MK ester A-600: manufactured by Shin-Nakamura Chemical Co., Ltd.)
4 Ethylene oxide (EO)-modified pentaerythritol tetraacrylate (4EO-PETTA) (SR494: manufactured by Sartomer)
(Monofunctional Acrylate Monomer)
Tetrahydrofurfuryl acrylate (THFA) (V#150: manufactured by Osaka Organic Chemical Industry Ltd.)
(Another Polyfunctional Monomer)
2-(2-Vinyloxyethoxy)ethyl acrylate (VEEA: manufactured by Nippon Shokubai Co., Ltd.)

It is noted that Tables 1 to 6 also show mass % of a total mass of polyfunctional (meth)acrylate monomers with respect to a total mass of photocurable compounds. (It is noted that the total mass of the photocurable compounds includes a mass of a photocurable compound contained in the pigment dispersion.)

[Photopolymerization Initiator]
DAROCURE TPO (manufactured by BASF Corporation)
IRGACURE 819 (manufactured by BASF Corporation)
[Fluorescent Brightener]
FLUORESCENT BRIGHTENER OB (manufactured by Xcolor Pigment) (in which A in general formula (1) has the structure of formula (4))
FLUORESCENT BRIGHTENER OB-1 (manufactured by Xcolor Pigment) (in which A in general formula (1) has the structure of formula (5))
FLUORESCENT BRIGHTENER PF (manufactured by Xcolor Pigment) (in which A in general formula (1) has the structure of formula (3))

FLUORESCENT BRIGHTENER PB (manufactured by Xcolor Pigment) (in which A in general formula (1) has the structure of formula (4))

FLUORESCENT BRIGHTENER KCB (manufactured by Xcolor Pigment) (in which A in general formula (1) has the structure of formula (2))

FLUORESCENT BRIGHTENER KSN (manufactured by Xcolor Pigment) (in which A in general formula (1) has the structure of formula (5))

FLUORESCENT BRIGHTENER FP-127 (manufactured by Xcolor Pigment) (stilbene-based compound)

[Antioxidant]

(Monofunctional Phenol-based Antioxidant)

IRGANOX 1520L (manufactured by BASF Corporation)
IRGANOX 1076 (manufactured by BASF Corporation)
(Polyfunctional Phenol-based Antioxidant)
NOCRAC NS-6 (manufactured by Ouchi Shinko Chemical Industrial Co., Ltd.)
SUMILIZER GS (manufactured by Sumitomo Chemical Co., Ltd.)
ADK STAB AO-40 (manufactured by ADEKA Corporation)
IRGANOX 1330 (manufactured by BASF Corporation)
(Phenol-based Antioxidant represented by General Formula (6))
IRGANOX 259 (manufactured by BASF Corporation)
IRGANOX 1035 (manufactured by BASF Corporation)
IRGANOX 1010 (manufactured by BASF Corporation)
(Phosphorus-based Antioxidant)
ADK STAB 1500 (manufactured by ADEKA Corporation)
(Sulfur-based Antioxidant)
ADK STAB AO-412A (manufactured by ADEKA Corporation)

[Gelling Agent]

Lauric acid amide (DIAMID Y: manufactured by Nippon Kasei Chemical Co., Ltd, carbon number: 12)
Stearyl stearate (Exepearl SS: manufactured by Kao Corporation, carbon numbers: 17-18)
Stearone (Kao Wax T-1: manufactured by Kao Corporation, carbon number: 17)

[Pigment Dispersion]

Cyan pigment dispersion prepared as described above

[Polymerization Inhibitor]

Irgastab UV10 (manufactured by BASF Corporation)

[Surfactant]

KF-352 (manufactured by Shin-Etsu Chemical Co., Ltd.)

Incidentally, for each of ink samples 1 to 24 and 26 to 31 containing the fluorescent brightener, a control ink having the same composition except that the fluorescent brightener is not contained was prepared. In the control ink, the amount of MPDDA was controlled so that the total mass of the ink be 100 mass %.

2. Formation of Image

[Image Forming Method]

Each of the sample inks and their control inks shown in Tables 1 to 6 was used for forming a solid image with a size of 5 cm×5 cm on coated paper A for printing (OK Top Coat, basis weight: 128 g/m$^2$, manufactured by Oji Paper Co., Ltd.) in the following manner:

As a discharge recording head of a line-type inkjet recording apparatus, a piezo head having a nozzle diameter of 20 μm and including 512 nozzles (in two rows each of 256 nozzles, arranged in a zigzag manner, nozzle pitch in each row: 360 dpi) was used. The temperature of the inkjet head was set to 80° C., and under discharging conditions for attaining an amount of every droplet of 2.5 pl, the ink was ejected at a rate of about 6 m/s, so as to record an image at resolution of 1,440 dpi×1,440 dpi. The recording rate was set to 500 mm/s. The formation of the image was carried out under an environment of 23° C. and 55% RH. It is noted that the term "dpi" refers to the number of dots per 2.54 cm.

After forming the image, the ink was cured by irradiating the image with ultraviolet rays using an LED lamp (manufactured by Phoseon Technology Inc., 395 nm, water-cooled LED) disposed in a downstream portion of the recording apparatus.

3. Evaluation of Image (Evaluation of Change in Glossiness of Image)

The 60°-glossiness of each solid image formed on the coated paper A for printing by using each of the ink samples and the control inks was measured using a gloss meter PG-II manufactured by Nippon Denshoku Industries Co., Ltd.

Next, a difference between the 60°-glossiness obtained using the ink sample and the 60°-glossiness obtained using the control ink was obtained as a glossiness change caused by the use of the fluorescent brightener. The thus obtained glossiness change was evaluated based on the following criteria.

Incidentally, ink 25 not containing the fluorescent brightener was evaluated as "D" (the glossiness of the image did not increase).

D: The glossiness of the image did not increase. (no effect)

C: Glossiness increase exceeded 0 and was less than 20.

B: Glossiness increase was 20 or more and less than 30.

A: Glossiness increase was 30 or more.

(Evaluation of Change in Image Color)

The b* value of each solid image formed on the coated paper A for printing by using each of the ink samples and the control inks was measured using a spectrophotometer FD-7, manufactured by Konica Minolta, Inc.

Next, a color difference ΔE between the L*a*b* value obtained using each ink sample and the b* value obtained using the corresponding control ink was obtained. The thus obtained color difference ΔE was evaluated based on the following criteria.

Incidentally, ink 19 not containing the fluorescent brightener was evaluated as "A" (the change in color could not be visually found).

D: The color difference ΔE exceeded 5. The change in color was largely found.

C: The color difference ΔE exceeded 3 and was 5 or less. The change in color was found.

B: The color difference ΔE was 1 or more and 3 or less. The change in color was slightly found but allowable.

A: The color difference ΔE was less than 1. The change in color was not visually found.

(Evaluation of Migration)

A solid image in the shape of a circle with a diameter of 10 cm was formed on coated paper A for printing in the above-described manner by using each ink sample, a PET film and a CPP film having a diameter of 10 cm were overlaid on the rear side of the image, and the resultant was wetted with 100 ml of a mixture of water and ethanol in a ratio of 5:95. Next, the mixture was put in a sealed vessel so as not to volatilize the mixture, and the resultant was allowed to stand still at 60° C. for 10 days. Thereafter, a total amount of components derived from the printed image (such as the photopolymerization initiator, the fluorescent brightener, and the antioxidant) contained in the mixture was calculated. The calculated component amount was defined as a migration amount, and was evaluated based on the following criteria:

D: The migration amount was 1,000 ppb or more.

C: The migration amount was 500 ppb or more and less than 1,000 ppb.

B: The migration amount was 100 ppb or more and less than 500 ppb.

A: The migration amount was less than 100 ppb.

The evaluation results are shown in Tables 1 to 6 below.

TABLE 1

| | Ink component | | Sample 1 | Sample 2 | Sample 3 | Sample 4 | Sample 5 | Sample 6 |
|---|---|---|---|---|---|---|---|---|
| Photocurable compound | Polyfunctional (meth)acrylate monomer | MPDDA | 31.7 | 34.3 | 30.8 | 33.4 | 45.8 | 43.4 |
| | | PO-NPGDA | 20.0 | 20.0 | 20.0 | 20.0 | | |
| | | PEG400DA | 20.0 | 20.0 | 20.0 | 20.0 | 20.0 | 20.0 |
| | | 4EO-PETTA | 10.0 | 10.0 | 10.0 | 10.0 | 10.0 | 10.0 |
| | Another polyfunctional monomer | VEEA | | | | | | |
| | Monofunctional acrylate monomer | V#150 | | | | | 10.0 | 10.0 |
| | Content of polyfunctional (meth)acrylate monomer | | 100.0 | 100.0 | 100.0 | 100.0 | 89.2 | 89.0 |
| Photopolymerization initiator | DAROCURE TPO | | 8.0 | | 8.0 | | 4.0 | |
| | IRGACURE 819 | | | 4.0 | | 4.0 | | 4.0 |
| Fluorescent brightener | FLUORESCENT BRIGHTENER OB | | 0.005 | | 1.0 | | 0.005 | |
| | FLUORESCENT BRIGHTENER OB-1 | | | 0.005 | | 1.0 | | 1.0 |
| | FLUORESCENT BRIGHTENER PF | | | | | | | |
| | FLUORESCENT BRIGHTENER PB | | | | | | | |
| | FLUORESCENT BRIGHTENER KCB | | | | | | | |
| | FLUORESCENT BRIGHTENER KSN | | | | | | | |
| | FLUORESCENT BRIGHTENER FP-127 | | | | | | | |
| Phenol-based antioxidant | Monofunctional | IRGANOX 1520L | 0.05 | | 0.05 | | 0.05 | |
| | | IRGANOX 1076 | | 1.5 | | 1.5 | | 1.5 |
| | Polyfunctional | Nocrac NS-6 | | | | | | |
| | | Sumilizer GS | | | | | | |
| | | Adk stab AO-40 | | | | | | |
| | | IRGANOX 1330 | | | | | | |
| | General formula (6) | IRGANOX 259 | | | | | | |
| | | IRGANOX 1035 | | | | | | |
| | | IRGANOX 1010 | | | | | | |
| | Pigment dispersion | | 10.0 | 10.0 | 10.0 | 10.0 | 10.0 | 10.0 |
| | Polymerization inhibitor | Irgastub UV-10 | 0.1 | 0.1 | 0.1 | 0.1 | 0.1 | 0.1 |
| | Surfactant | KF-352 | 0.1 | 0.1 | 0.1 | 0.1 | 0.1 | 0.1 |
| | Total mass % of ink | | 100.0 | 100.0 | 100.0 | 100.0 | 100.0 | 100.0 |
| Evaluation | Change in glossiness | | C | C | B | B | C | B |
| | Change in color | | B | B | C | C | B | C |
| | Migration | | C | C | C | C | C | C |

TABLE 2

| | Ink component | | Sample 7 | Sample 8 | Sample 9 | Sample 10 |
|---|---|---|---|---|---|---|
| Photocurable compound | Polyfunctional (meth)acrylate monomer | MPDDA | 31.3 | 34.9 | 31.5 | 34.1 |
| | | PO-NPGDA | 20.0 | 20.0 | 20.0 | 20.0 |
| | | PEG400DA | 20.0 | 20.0 | 20.0 | 20.0 |
| | | 4EO-PETTA | 10.0 | 10.0 | 10.0 | 10.0 |
| | Another polyfunctional monomer | VEEA | | | | |
| | Monofunctional acrylate monomer | V#150 | | | | |
| | Content of polyfunctional (meth)acrylate monomer | | 100.0 | 100.0 | 100.0 | 100.0 |
| Photopolymerization initiator | DAROCURE TPO | | 8.0 | | 8.0 | |
| | IRGACURE 819 | | | 4.0 | | 4.0 |
| Fluorescent brightener | FLUORESCENT BRIGHTENER OB | | 0.01 | | 0.3 | |
| | FLUORESCENT BRIGHTENER OB-1 | | | 0.5 | | 0.3 |
| | FLUORESCENT BRIGHTENER PF | | | | | |
| | FLUORESCENT BRIGHTENER PB | | | | | |
| | FLUORESCENT BRIGHTENER KCB | | | | | |
| | FLUORESCENT BRIGHTENER KSN | | | | | |
| | FLUORESCENT BRIGHTENER FP-127 | | | | | |
| Phenol-based antioxidant | Monofunctional | IRGANOX 1520L | 0.5 | | 0.05 | |
| | | IRGANOX 1076 | | 0.5 | | 1.5 |
| | Polyfunctional | Nocrac NS-6 | | | | |
| | | Sumilizer GS | | | | |
| | | Adk stab AO-40 | | | | |
| | | IRGANOX 1330 | | | | |
| | General formula (6) | IRGANOX 259 | | | | |
| | | IRGANOX 1035 | | | | |
| | | IRGANOX 1010 | | | | |

TABLE 2-continued

| | Ink component | | Sample 7 | Sample 8 | Sample 9 | Sample 10 |
|---|---|---|---|---|---|---|
| | Pigment dispersion | | 10.0 | 10.0 | 10.0 | 10.0 |
| | Polymerization inhibitor | Irgastub UV-10 | 0.1 | 0.1 | 0.1 | 0.1 |
| | Surfactant | KF-352 | 0.1 | 0.1 | 0.1 | 0.1 |
| | Total mass % of ink | | 100.0 | 100.0 | 100.0 | 100.0 |
| Evaluation | Change in glossiness | | B | B | B | B |
| | Change in color | | B | B | B | B |
| | Migration | | C | C | C | C |

TABLE 3

| | Ink component | | Sample 11 | Sample 12 | Sample 13 | Sample 14 |
|---|---|---|---|---|---|---|
| Photocurable compound | Polyfunctional (meth)acrylate monomer | MPDDA | 31.5 | 34.6 | 31.1 | 35.1 |
| | | PO-NPGDA | 20.0 | 20.0 | 20.0 | 20.0 |
| | | PEG400DA | 20.0 | 20.0 | 20.0 | 20.0 |
| | | 4EO-PETTA | 10.0 | 10.0 | 10.0 | 10.0 |
| | Another polyfunctional monomer | VEEA | | | | |
| | Monofunctional acrylate monomer | V#150 | | | | |
| | Content of polyfunctional (meth)acrylate monomer | | 100.0 | 100.0 | 100.0 | 100.0 |
| Photopolymerization initiator | DAROCURE TPO | | 8.0 | | 8.0 | |
| | IRGACURE 819 | | | 4.0 | | 4.0 |
| Fluorescent brightener | FLUORESCENT BRIGHTENER OB | | 0.3 | | 0.3 | |
| | FLUORESCENT BRIGHTENER OB-1 | | | 0.3 | | 0.3 |
| | FLUORESCENT BRIGHTENER PF | | | | | |
| | FLUORESCENT BRIGHTENER PB | | | | | |
| | FLUORESCENT BRIGHTENER KCB | | | | | |
| | FLUORESCENT BRIGHTENER KSN | | | | | |
| | FLUORESCENT BRIGHTENER FP-127 | | | | | |
| Phenol-based antioxidant | Monofunctional | IRGANOX 1520L | 0.1 | | 0.5 | |
| | | IRGANOX 1076 | | 1.0 | | 0.5 |
| | Polyfunctional | Nocrac NS-6 | | | | |
| | | Sumilizer GS | | | | |
| | | Adk stab AO-40 | | | | |
| | | IRGANOX 1330 | | | | |
| | General formula (6) | IRGANOX 259 | | | | |
| | | IRGANOX 1035 | | | | |
| | | IRGANOX 1010 | | | | |
| | Pigment dispersion | | 10.0 | 10.0 | 10.0 | 10.0 |
| | Polymerization inhibitor | Irgastub UV-10 | 0.1 | 0.1 | 0.1 | 0.1 |
| | Surfactant | KF-352 | 0.1 | 0.1 | 0.1 | 0.1 |
| | Total mass % of ink | | 100.0 | 100.0 | 100.0 | 100.0 |
| Evaluation | Change in glossiness | | B | B | B | B |
| | Change in color | | A | A | A | A |
| | Migration | | C | C | C | C |

TABLE 4

| | Ink component | | Sample 15 | Sample 16 | Sample 17 | Sample 18 |
|---|---|---|---|---|---|---|
| Photocurable compound | Polyfunctional (meth)acrylate monomer | MPDDA | 31.1 | 35.1 | 31.1 | 35.1 |
| | | PO-NPGDA | 20.0 | 20.0 | 20.0 | 20.0 |
| | | PEG400DA | 20.0 | 20.0 | 20.0 | 20.0 |
| | | 4EO-PETTA | 10.0 | 10.0 | 10.0 | 10.0 |
| | Another polyfunctional monomer | VEEA | | | | |
| | Monofunctional acrylate monomer | V#150 | | | | |
| | Content of polyfunctional (meth)acrylate monomer | | 100.0 | 100.0 | 100.0 | 100.0 |
| Photopolymerization initiator | DAROCURE TPO | | 8.0 | | 8.0 | |
| | IRGACURE 819 | | | 4.0 | | 4.0 |
| Fluorescent brightener | FLUORESCENT BRIGHTENER OB | | | | | |
| | FLUORESCENT BRIGHTENER OB-1 | | | | | |
| | FLUORESCENT BRIGHTENER PF | | 0.3 | | | |
| | FLUORESCENT BRIGHTENER PB | | | 0.3 | | |

TABLE 4-continued

| | Ink component | | Sample 15 | Sample 16 | Sample 17 | Sample 18 |
|---|---|---|---|---|---|---|
| | FLUORESCENT BRIGHTENER KCB | | | | 0.3 | |
| | FLUORESCENT BRIGHTENER KSN | | | | | 0.3 |
| | FLUORESCENT BRIGHTENER FP-127 | | | | | |
| Phenol-based antioxidant | Monofunctional | IRGANOX 1520L | | | | |
| | | IRGANOX 1076 | | | | |
| | Polyfunctional | Nocrac NS-6 | 0.5 | | | |
| | | Sumilizer GS | | 0.5 | | |
| | | Adk stab AO-40 | | | 0.5 | |
| | | IRGANOX 1330 | | | | 0.5 |
| | General formula (6) | IRGANOX 259 | | | | |
| | | IRGANOX 1035 | | | | |
| | | IRGANOX 1010 | | | | |
| | Pigment dispersion | | 10.0 | 10.0 | 10.0 | 10.0 |
| | Polymerization inhibitor | Irgastub UV-10 | 0.1 | 0.1 | 0.1 | 0.1 |
| | Surfactant | KF-352 | 0.1 | 0.1 | 0.1 | 0.1 |
| | Total mass % of ink | | 100.0 | 100.0 | 100.0 | 100.0 |
| Evaluation | Change in glossiness | | B | B | B | B |
| | Change in color | | A | A | A | A |
| | Migration | | B | B | B | B |

TABLE 5

| | Ink component | | Sample 19 | Sample 20 | Sample 21 | Sample 22 | Sample 23 | Sample 24 |
|---|---|---|---|---|---|---|---|---|
| Photocurable compound | Polyfunctional (meth)acrylate monomer | MPDDA | 31.1 | 35.1 | 31.1 | 33.1 | 29.1 | 33.1 |
| | | PO-NPGDA | 20.0 | 20.0 | 20.0 | 20.0 | 20.0 | 20.0 |
| | | PEG400DA | 20.0 | 20.0 | 20.0 | 20.0 | 20.0 | 20.0 |
| | | 4EO-PETTA | 10.0 | 10.0 | 10.0 | 10.0 | 10.0 | 10.0 |
| | Another polyfunctional monomer | VEEA | | | | | | |
| | Monofunctional acrylate monomer | V#150 | | | | | | |
| | Content of polyfunctional (meth)acrylate monomer | | 100.0 | 100.0 | 100.0 | 100.0 | 100.0 | 100.0 |
| Photopolymerization initiator | DAROCURE TPO | | 8.0 | | 8.0 | | 8.0 | |
| | IRGACURE 819 | | | 4.0 | | 4.0 | | 4.0 |
| Fluorescent brightener | FLUORESCENT BRIGHTENER OB | | 0.3 | | | | | |
| | FLUORESCENT BRIGHTENER OB-1 | | | 0.3 | | | | |
| | FLUORESCENT BRIGHTENER PF | | | | 0.3 | | | |
| | FLUORESCENT BRIGHTENER PB | | | | | 0.3 | | |
| | FLUORESCENT BRIGHTENER KCB | | | | | | 0.3 | |
| | FLUORESCENT BRIGHTENER KSN | | | | | | | 0.3 |
| | FLUORESCENT BRIGHTENER FP-127 | | | | | | | |
| Phenol-based antioxidant | Monofunctional | IRGANOX 1520L | | | | | | |
| | | IRGANOX 1076 | | | | | | |
| | Polyfunctional | Nocrac NS-6 | | | | | | |
| | | Sumilizer GS | | | | | | |
| | | Adk stab AO-40 | | | | | | |
| | | IRGANOX 1330 | | | | | | |
| | General formula (6) | IRGANOX 259 | 0.5 | | | 0.5 | | |
| | | IRGANOX 1035 | | 0.5 | | | 0.5 | |
| | | IRGANOX 1010 | | | 0.5 | | | 0.5 |
| Gelling agent | Lauryl acid amide | | | | | 2.0 | | |
| | Stearyl stearate | | | | | | 2.0 | |
| | Stearone | | | | | | | 2.0 |
| | Pigment dispersion | | 10.0 | 10.0 | 10.0 | 10.0 | 10.0 | 10.0 |
| | Polymerization inhibitor | Irgastub UV-10 | 0.1 | 0.1 | 0.1 | 0.1 | 0.1 | 0.1 |
| | Surfactant | KF-352 | 0.1 | 0.1 | 0.1 | 0.1 | 0.1 | 0.1 |
| | Total parts by weight of ink | | 100.0 | 100.0 | 100.0 | 100.0 | 100.0 | 100.0 |
| Evaluation | Change in glossiness | | B | B | B | A | A | A |
| | Change in color | | A | A | A | A | A | A |
| | Migration | | A | A | A | A | A | A |

TABLE 6

| Ink component | | | Sample 25 | Sample 26 | Sample 27 | Sample 28 | Sample 29 | Sample 30 | Sample 31 |
|---|---|---|---|---|---|---|---|---|---|
| Photocurable compound | Polyfunctional (meth)acrylate monomer | MPDDA | 31.3 | 35.6 | 31.1 | 35.1 | 31.1 | 35.1 | 35.1 |
| | | PO-NPGDA | 20.0 | 20.0 | | | 20.0 | 20.0 | 20.0 |
| | | PEG400DA | 20.0 | 20.0 | 20.0 | 20.0 | 20.0 | 20.0 | 20.0 |
| | | 4EO-PETTA | 10.0 | 10.0 | 10.0 | 10.0 | 10.0 | 10.0 | 10.0 |
| | Another polyfunctional monomer | VEEA | | | 20.0 | | | | |
| | Monofunctional acrylate monomer | V#150 | | | | 20.0 | | | |
| | Content of polyfunctional (meth)acrylate monomer | | 100.0 | 100.0 | 77.3 | 78.3 | 100.0 | 100.0 | 100.0 |
| Photopolymerization initiator | DAROCURE TPO | | 8.0 | | 8.0 | | 8.0 | | |
| | IRGACURE 819 | | | 4.0 | | 4.0 | | 4.0 | 4.0 |
| Fluorescent brightener | FLUORESCENT BRIGHTENER OB | | | 0.3 | | | | | |
| | FLUORESCENT BRIGHTENER OB-1 | | | | 0.3 | | | | |
| | FLUORESCENT BRIGHTENER PF | | | | | 0.3 | | | |
| | FLUORESCENT BRIGHTENER PB | | | | | | 0.3 | | |
| | FLUORESCENT BRIGHTENER KCB | | | | | | | 0.3 | |
| | FLUORESCENT BRIGHTENER KSN | | | | | | | | |
| | FLUORESCENT BRIGHTENER FP-127 | | | | | | | | 0.3 |
| Phenol-based antioxidant | Monofunctional | IRGANOX 1520L | | | | | | | |
| | | IRGANOX 1076 | | | | | | | |
| | Polyfunctional | Nocrac NS-6 | | | | | | | |
| | | Sumilizer GS | | | | | | | |
| | | Adk stab AO-40 | | | | | | | |
| | | IRGANOX 1330 | | | | | | | |
| | General formula (6) | IRGANOX 259 | 0.5 | | | | | | |
| | | IRGANOX 1035 | | | 0.5 | | | | |
| | | IRGANOX 1010 | | | | 0.5 | | | |
| Phosphorus-based antioxidant | | Adk stab 1500 | | | | | 0.5 | | |
| Sulfur-based antioxidant | | Adk stab AO-412S | | | | | | 0.5 | 0.5 |
| Pigment dispersion | | | 10.0 | 10.0 | 10.0 | 10.0 | 10.0 | 10.0 | 10.0 |
| Polymerization inhibitor | | Irgastub UV-10 | 0.1 | 0.1 | 0.1 | 0.1 | 0.1 | 0.1 | 0.1 |
| Surfactant | | KF-352 | 0.1 | 0.1 | 0.1 | 0.1 | 0.1 | 0.1 | 0.1 |
| | Total parts by weight of ink | | 100.0 | 100.0 | 100.0 | 100.0 | 100.0 | 100.0 | 100.0 |
| Evaluation | Change in glossiness | | D | C | D | C | D | D | C |
| | Change in color | | C | C | B | B | B | B | D |
| | Migration | | C | D | D | D | D | D | D |

According to the results shown in Tables 1 to 5, in all the images formed by using the inks of the present invention each containing the photocurable compound containing the (meth)acrylate having two or more (meth)acryloyl groups in an amount of 80 mass % or more with respect to the total mass of the photocurable compound, the photopolymerization initiator, the fluorescent brightener represented by general formula (1), and the phenol-based antioxidant, the glossiness increased (namely, the change in glossiness was good), the change in color was small, and the migration was suppressed.

According to the results shown in Table 2, in using samples 7 to 10 in each of which the content of the fluorescent brightener is 0.01 mass % or more, the change in glossiness was improved as compared with that obtained by using samples 1, 2 and 5 of Table 1 respectively having the same compositions in which the content of the fluorescent brightener was less than 0.01 mass % (specifically, was 0.005 mass %). Besides, the change in color was improved as compared with that obtained by using samples 3, 4 and 6 of Table 1 in each of which the content of the fluorescent brightener exceeded 0.5 mass % (specifically, was 1.0 mass %).

In using samples 11 to 14 of Table 3 in each of which the content of the phenol-based antioxidant was 0.1 mass % or more and 1.0 mass % or less, the change in color was further improved as compared with that obtained by using sample 9 of Table 2 having the same composition in which the content of the antioxidant was less than 0.1 mass % (specifically, was 0.05 mass %) and sample 10 of Table 2 in which the content of the antioxidant exceeded 1.0 mass % (specifically, was 1.5 mass %). Besides, in the images formed by using samples 15 to 18 of Table 4 in each of which the polyfunctional compound was used as the antioxidant, the migration was suppressed. Furthermore, in the images formed by using samples 19 to 21 of Table 5 in each of which the compound of general formula (6) was used as the antioxidant, the migration was further suppressed.

In using samples 22 to 24 in each of which the compound of general formula (1) was used as the fluorescent brightener, the compound of general formula (6) was used as the antioxidant, and the gelling agent was further contained, the change in glossiness was further improved as compared with that obtained by using samples 19 to 21 of Table 5 having the same composition but not containing the gelling agent. Specifically, in the images formed by using the control inks of samples 22 to 24 not containing the fluorescent brightener, the glossiness was lowered, owing to the gelling agent, as compared with that obtained by using the control inks of samples 19 to 21 not containing the gelling agent, but in the images formed by using samples 22 to 24, the difference in the glossiness from that obtained by using the control ink is increased, and hence the evaluation of the change in glossiness was improved. This reveals that the ink composition of the present invention is effective also in an ink containing a gelling agent.

According to the results shown in Table 6, sample 25 containing the photocurable compound merely containing the (meth)acrylate having two or more (meth)acryloyl groups and the antioxidant of general formula (6) but not containing the fluorescent brightener was evaluated as poor in the change in glossiness, and sample 31 containing the fluorescent brightener having a structure different from the structure of general formula (1) (i.e., the stilbene-based fluorescent brightener) as the fluorescent brightener was evaluated as poor in the change in color and the migration. On the other hand, sample 26 containing the photocurable compound and the fluorescent brightener of general formula (1) but not containing the antioxidant was evaluated as poor in the migration. Besides, samples 29 and 30 each containing the photocurable compound and the fluorescent brightener and containing the antioxidant different from the phenol-based antioxidant were evaluated as poor in the change in glossiness and the migration.

Besides, in using sample 27 in which the fluorescent brightener of general formula (1) and the antioxidant of general formula (6) were contained but the photocurable compound contained a polyfunctional monomer in addition to the (meth)acrylate, and the amount of the (meth)acrylate was less than 80 mass %, although the change in color was suppressed, the change in glossiness and the migration were evaluated as poor. Similarly, in using sample 28 of Table 6 in which the fluorescent brightener of general formula (1) and the antioxidant of general formula (6) were contained but the photocurable compound contained a monofunctional monomer, and the amount of the (meth)acrylate was less than 80 mass %, although the change in color was suppressed and the change in glossiness was improved, the migration was evaluated as poor.

The results of comparative examples shown in Table 6 reveal that the glossiness of an image is improved and the change in color and the migration are suppressed by the interaction among the fluorescent brightener of general formula (1), the phenol-based antioxidant, and the (meth)acrylate having two or more (meth)acryloyl groups.

INDUSTRIAL APPLICABILITY

Using the ink of the present invention enables forming an image having high glossiness with migration suppressed. Therefore, the present invention is expected to broaden the range of applications of an actinic radiation-curable inkjet ink and contribute to the development and dissemination of the technology in the technical field.

Although embodiments of the present invention have been described and illustrated in detail, it is clearly understood that the same is by way of illustration and example only and not limitation, the scope of the present invention should be interpreted by terms of the appended claims.

What is claimed is:

1. An actinic radiation-curable inkjet ink, comprising a photocurable compound, a polymerization initiator, a fluorescent brightener, an antioxidant, and a gelling agent, wherein the fluorescent brightener is a compound represented by the following general formula (1):

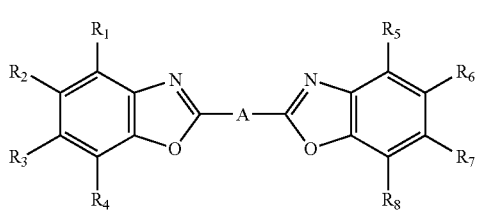

wherein $R_1$ to $R_8$ each independently represent a hydrogen atom or an alkyl group, adjacent substituents of $R_1$ to $R_8$ optionally forming a ring, and A represents a linking group represented by any one of the following formulas (2) to (5):

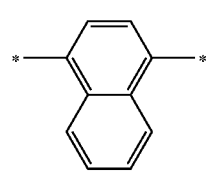

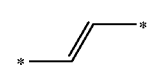

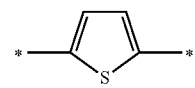

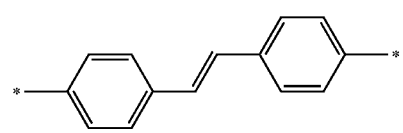

wherein each * represents a bonding position of A of each formula;

the antioxidant is a phenol-based antioxidant; and the photocurable compound contains a (meth)acrylate having two or more (meth)acryloyl groups in an amount of 80 mass % or more with respect to a total mass of the photocurable compound.

2. The actinic radiation-curable inkjet ink according to claim 1, wherein a content of the fluorescent brightener is 0.01 mass % or more and 0.5 mass % or less with respect to a total mass of the actinic radiation-curable inkjet ink.

3. The actinic radiation-curable inkjet ink according to claim 1, wherein a content of the antioxidant is 0.1 mass % or more and 1.0 mass % or less with respect to a total mass of the actinic radiation-curable inkjet ink.

4. The actinic radiation-curable inkjet ink according to claim 1, wherein the antioxidant is a polyfunctional phenol-based antioxidant.

5. The actinic radiation-curable inkjet ink according to claim 4, wherein the antioxidant is a compound represented by the following general formula (6):

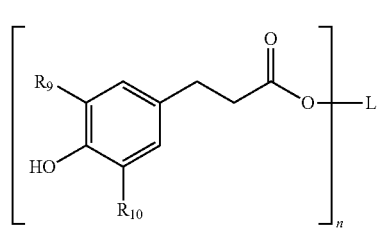

wherein $R_9$ and $R_{10}$ each independently represent an alkyl group having 1 or more and 4 or less carbon atoms, n represents an integer of 2 to 4, and L represents an alkyl group having 1 or more and 10 or less carbon atoms.

6. The actinic radiation-curable inkjet ink according to claim 1,
wherein the gelling agent contains a compound represented by the following general formula (G1) or a compound represented by the following general formula (G2):

$$R_{11}\text{—CO—}R_{12} \quad \text{General Formula (G1):}$$

$$R_{13}\text{—COO—}R_{14} \quad \text{General formula (G2):}$$

wherein $R_{11}$ and $R_{12}$ each independently represent a straight chain hydrocarbon group having 9 or more and 25 or less carbon atoms.

7. The actinic radiation-curable inkjet ink according to claim 1, further comprising a colorant.

8. An image forming method, comprising:
discharging a droplet of the actinic radiation-curable inkjet ink according to claim 1 from a nozzle of an inkjet head and causing the droplet to land on a substrate; and
curing the actinic radiation-curable inkjet ink by irradiating, with actinic radiation, the droplet of the actinic radiation-curable inkjet ink landed on the substrate.

\* \* \* \* \*